United States Patent [19]
Drevillon et al.

[11] Patent Number: 5,536,936
[45] Date of Patent: Jul. 16, 1996

[54] SPECTROSCOPIC ELLIPSOMETER MODULATED BY AN EXTERNAL EXCITATION

[75] Inventors: Bernard Drevillon, Meudon; Jean-Yves Parey, la Ville du Bois; Razvigor Ossikovski, Palaiseau Cedex, all of France

[73] Assignee: Centre National de la Recherche, Paris, France

[21] Appl. No.: 373,933

[22] Filed: Jan. 11, 1995

[30] Foreign Application Priority Data

Jan. 12, 1994 [FR] France .................. 94 00285

[51] Int. Cl.$^6$ ............................. G01J 3/50
[52] U.S. Cl. ............... 250/226; 250/559.22; 356/432
[58] Field of Search .................. 250/226, 559.22, 250/559.27, 559.49; 356/432 T, 369, 367

[56] References Cited

U.S. PATENT DOCUMENTS

| | | | |
|---|---|---|---|
| 4,211,488 | 7/1980 | Kleinknecht | 356/432 T |
| 4,632,561 | 12/1986 | Rosencwaig et al. | 356/432 T |
| 4,866,264 | 9/1989 | Biricik et al. | 250/225 |
| 5,329,357 | 7/1994 | Bernoux et al. | 356/369 |

FOREIGN PATENT DOCUMENTS 2685962 7/1993 France.

OTHER PUBLICATIONS

"Modulated Ellipsometry for Characterization of Multiple Quantum Wells and Superlattices," by Zettler et al., Thin Solid Films, vol. 233, Nos. ½, Oct. 12, 1993, pp. 112–116.

"Modulated Ellipsometric Measurements and Transfer–Matrix Calculation of the Field–Dependent Dielectric Function of a Multiple Quantum Well," by Zettler et al., Physical Review, vol. 46, No. 24, Dec. 15, 1992, pp. 15955–15962.

"Electroreflectance in a Nonuniform Field in the Small Wave–Number Approximation and its Measurement by Ellipsometry," by Yang et al., Physical Review, vol. 5, No. 6, Mar. 15, 1972, pp. 2242–2250.

"Ellipsometric Measurement of the Kerr Magnetooptic Effect," by Minden, Applied Optics, vol. 18, No. 6, Mar. 15, 1979, pp. 813–817.

"Design of New In Situ Spectroscopic Phase Modulated Ellipsometer," by Benferhat, Le Vide, Les Couches Minces, vol. 47, No. 258, Aug./Sep./Oct. 1991, pp. 264–273.

*Primary Examiner*—Stephone Allen
*Assistant Examiner*—Que T. Le
*Attorney, Agent, or Firm*—Popham, Haik, Schnobrich & Kaufman, Ltd.

[57] ABSTRACT

This invention concerns a spectroscopic ellipsometer modulated at a frequency ($\omega_m$) intended for taking measurements of a sample (3). The spectroscopic ellipsometer is phase modulated, the sample being excited by external means (16) producing periodic, alternating excitation at a frequency ($\Omega_e$). The measurement contains the ellipsometric parameter values ($\psi$, $\Delta$) of the sample, respectively in the presence of ($\psi_1$, $\Delta_1$) and in the absence of ($\psi_2$, $\Delta_2$) excitation of the sample, as a function of excitation frequency ($\Omega_e$).

17 Claims, 2 Drawing Sheets

SPECTROSCOPIC ELLIPSOMETER MODULATED BY AN EXTERNAL EXCITATION

BACKGROUND OF THE INVENTION

1. Field of the Invention

This invention concerns a modulated spectroscopic ellipsometer.

2. Background Information

Ellipsometry is a non-destructive measuring technique allowing optical characterization of a sample having a specular or almost specular surface.

Ellipsometry can be performed in situ, and may therefore be used to study mechanisms of thin film growth and interface formation, and the control of the development processes of these films and interfaces. Ellipsometry is used, for example, to study and control semiconductor fabrication.

Ellipsometric measurements can be taken at a fixed or variable wavelength (spectroscopic ellipsometry). They form part of the group of specular measurement techniques, which includes for example reflectance, modulated reflectance (electroreflectance, photoreflectance), anisotropic reflectance (spectroscopic differential reflectance), absorption and transmission measurements, with which they can be associated. An ellipsometric measurement is taken by illuminating the surface of a sample with a light beam and comparing the polarization state of the reflected or transmitted light beam r to that of the incident beam i. The polarization vector E is generally represented by its projections $E_s$ and $E_p$, respectively perpendicular and parallel to the incidence plane; $E_p$ and $E_s$ are complex amplitudes.

In the field of ellipsometry, the ratio $(E_p/E_s)^r / (E_p/E_s)^i$ denoting the changes in the polarization state produced by the surface studied is generally represented in the following form:

$$tg\psi \cdot \exp(i\Delta) = (E_p/E_s)^r / (E_p/E_s)^i$$

The object of ellipsometry is therefore to measure the parameters $\psi$ and $\Delta$ for a given surface.

The wavelength domain and the various conditions for taking the measurement, such as the polarization modulation frequency, and in turn the apparatus and ellipsometers to be used, are determined from the materials or phenomena to be studied.

French patent FR-A-2.602.338 describes a phase-modulated, Fourier-transform, infrared ellipsometer.

Physicists have recently discovered the interest of characterizing films and stacked films or interfaces by means of ellipsometric measurements taken in the presence or absence of external excitation and in comparing the measurements obtained in the presence or absence of excitation.

This excitation can, for example, be thermal, optical, electrical or magnetic.

For more details on this subject, the reader is invited to refer to the article "Modulated Ellipsometric Measurements and Transfer-matrix Calculation of the Field-dependent Dielectric Function of a Multiple Quantum Well" by J.-Th. Zettler (The American Physical Society—Phys. Rev. B46, 15955–1992) and to the article "Photoellipsometry Determination of Surface Fermi Level in GaAs (100)" extract from the Journal of Vacuum Science Technology A 11(4), July/August 1993, by Yi-Ming Xiong.

SUMMARY OF THE INVENTION

The object of the present invention is a spectroscopic ellipsometer for measuring the ellipsometric parameters of a sample in the presence or absence of excitation.

A further object of the invention is to propose such an ellipsometer offering greater measuring accuracy than any currently known device.

Moreover, it was also noted that the ellipsometric parameters measured in the presence and in the absence of external excitation depend on the frequency at which periodic excitation is applied.

A further object of the invention is to allow measurement of the sample's ellipsometric parameters as a function of excitation frequency.

To achieve this, the invention concerns a spectroscopic ellipsometer modulated at a frequency $\omega_m$ intended to measure a sample, comprising a spectroscopic ellipsometer, equipped with electronic processing means and supplying ellipsometric parameters, and external means for exciting the sample.

The modulation at the frequency $\omega_m$ is the modulation of the incident beam or reflected beam usually implemented in spectroscopic ellipsometers.

According to the invention, the spectroscopic ellipsometer is phase-modulated, the means for exciting the sample producing periodic, alternating excitation at a frequency $\Omega_e$, a reference of which being sent to the electronic processing means. The measurement contains the values of the sample's ellipsometric parameters, respectively in the presence and absence of excitation of the sample, as a function of the external excitation frequency.

The accuracy of the measurement is enhanced when the electric signal from the photodetector, processed by the electronic processing means, comprises zones significant of excitation, zones significant of non-excitation and transition zones separating the significant zones, the transition zones being neutralized and the significant zones being used to produce the ellipsometric parameters of the sample, respectively in the presence and absence of external excitation, as a function of the external excitation frequency.

Advantageously, the electronic processing means conduct tests on the state of the excitation means.

Preferably, the excitation frequency $\omega_e$ is low compared to modulation frequency $\omega_m$, the electronic processing means being synchronized on the external excitation and the electric signal of the photodetector being acquired by the electronic processing means after a whole number t of modulation periods, starting from a positive-going transition of the excitation signal, for a number T of modulation periods to produce the ellipsometric parameters in the presence of excitation, then after a number t of modulation periods, starting from a negative-going transition of the excitation signal, for a number T of modulation periods to produce the ellipsometric parameters in the absence of excitation, the value of T being:

$$\left( \left[ \frac{\omega_m}{\Omega_e \times 2} \right] - 2t \right)$$

where the expression $$\left[ \frac{\omega_m}{\Omega_e \times 2} \right]$$

designates the integer part of $$\frac{\omega_m}{\Omega_e \times 2}$$

Indeed throughout this text, square brackets [ ] are used to designate the integer part of the expression that they contain.

Advantageously, a check is conducted by a test of the level of the excitation signal, conducted in the region of each positive-going and negative-going transition.

The introduction of a third modulation, formed by switching the light beam of the spectroscopic ellipsometer at a frequency $\omega_c$ located between modulation frequency $\omega_m$ of the ellipsometer and excitation frequency $\Omega_e$, provides a means of improving the accuracy of the parameters measured. A reference of the switching frequency is sent to the electronic processing means.

The excitation of the sample can be obtained by various physical phenomena, for example luminous, electric, magnetic, thermal, etc.

Good accuracy is obtained, without switching the ellipsometer's light beam, using a modulation frequency in the order of 50 kHz and an excitation frequency in the order of 5 kHz.

BRIEF DESCRIPTION OF THE DRAWINGS

The invention will now be described in detail with reference to the attached drawings, in which.

Common elements have been assigned the same reference numbers in FIGS. 1 and 3 and FIGS. 2 and 4, respectively.

DESCRIPTION OF THE PREFERRED EMBODIMENTS

Figure 1:
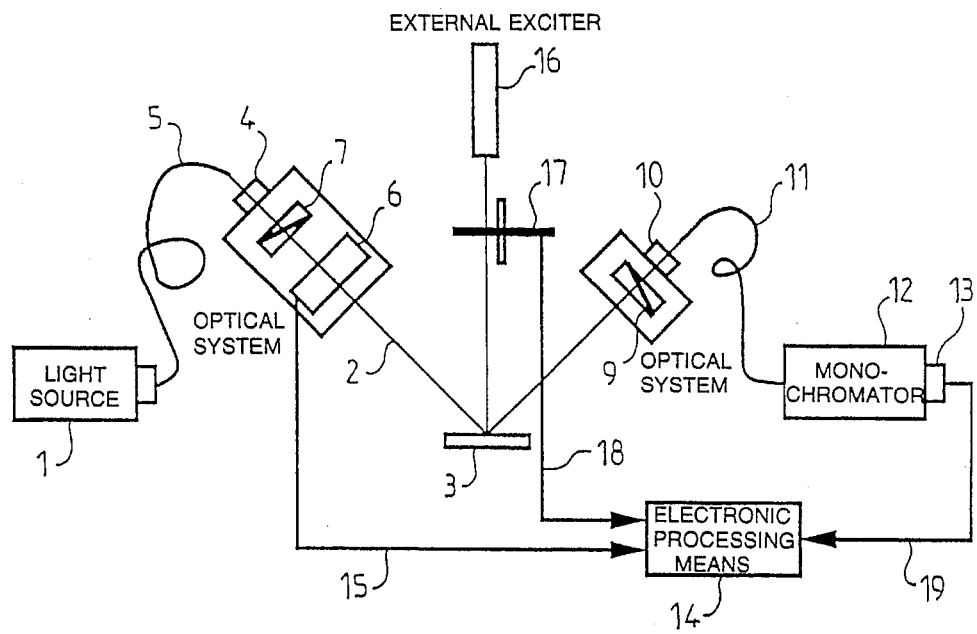
FIG. 1 is a general diagram of the ellipsometer of the invention with double modulation.

A light source 1 emits a light beam 2 directed onto a sample 3 by an optical system 4. Optical system 4 is possibly coupled to source 1 by means of an optical fiber 5.

Light beam 2 is phase modulated by means of a photoelastic modulator 6 placed after a polarizer 7. After being reflected from the sample, light beam 8 is analyzed by an analyzer 9 and recovered by an optical system 10 which, possibly by use of an optical fiber 11, sends it onto a monochromator 12. The intensity of the flux transmitted by the monochromator is converted by a detector 13 into an electric signal which is supplied to electronic processing means 14, comprising in particular a computer.

Electronic processing means 14 also receive a frequency and phase reference from the photoelastic modulator via a line 15.

Light source 1 is an extended spectrum source in the considered wavelength domain in which it is desired to take measurements of the ellipsometric parameters of sample 3.

Sample 3 receives an external periodic excitation from external exciter 16 whose effect is modulated by a switching device 17 at a frequency $\Omega_e$. A phase and frequency reference signal of the switching of switching device 17 is sent to electronic processing means 14 via line 18.

A connection 19 connects detector 13 to electronic processing means 14.

Figure 2:
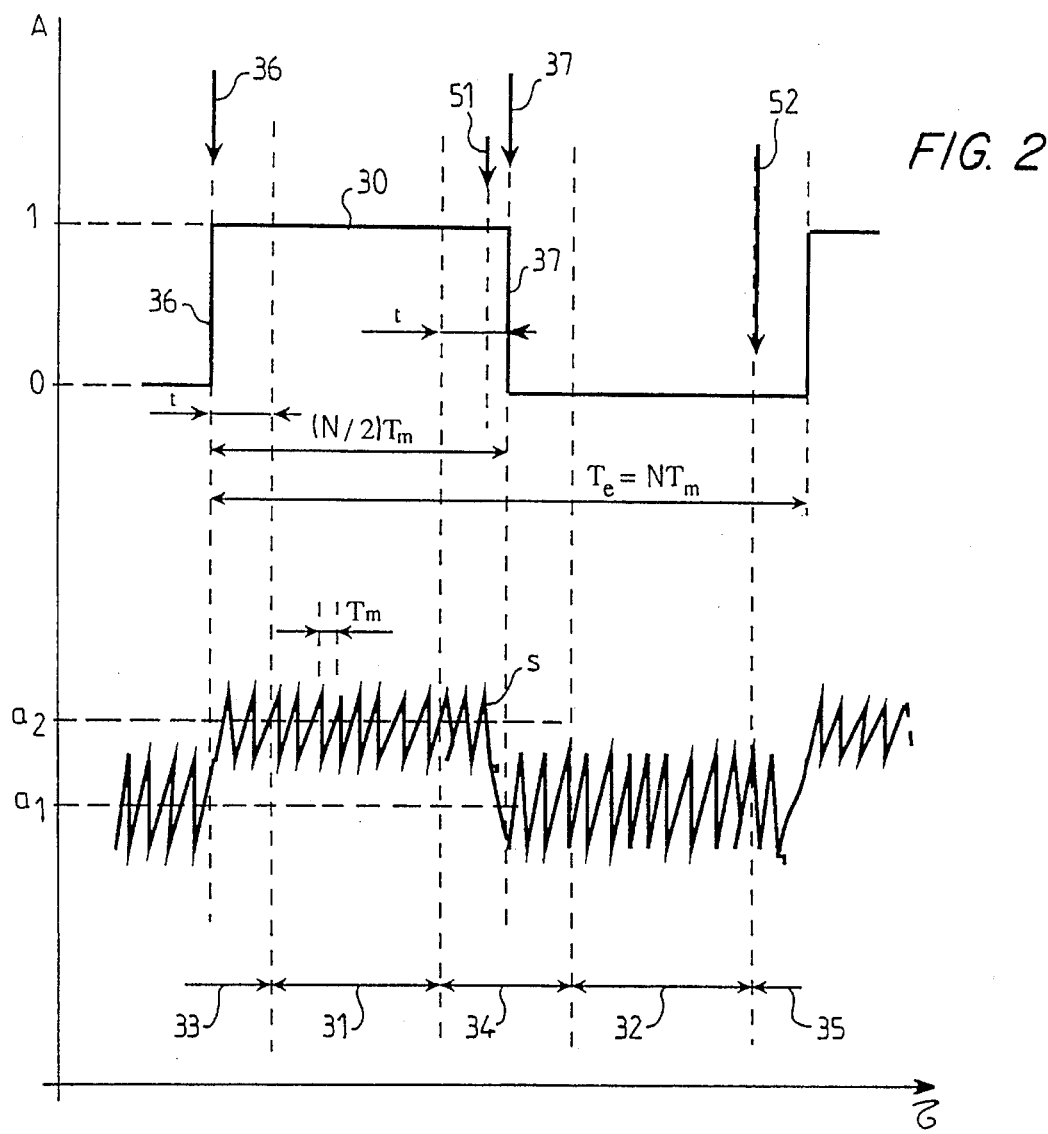
FIG. 2 is a timing diagram of the electric signal furnished by the photodetector compared to the excitation signal in the ellipsometer of FIG. 1.
Figure 4:
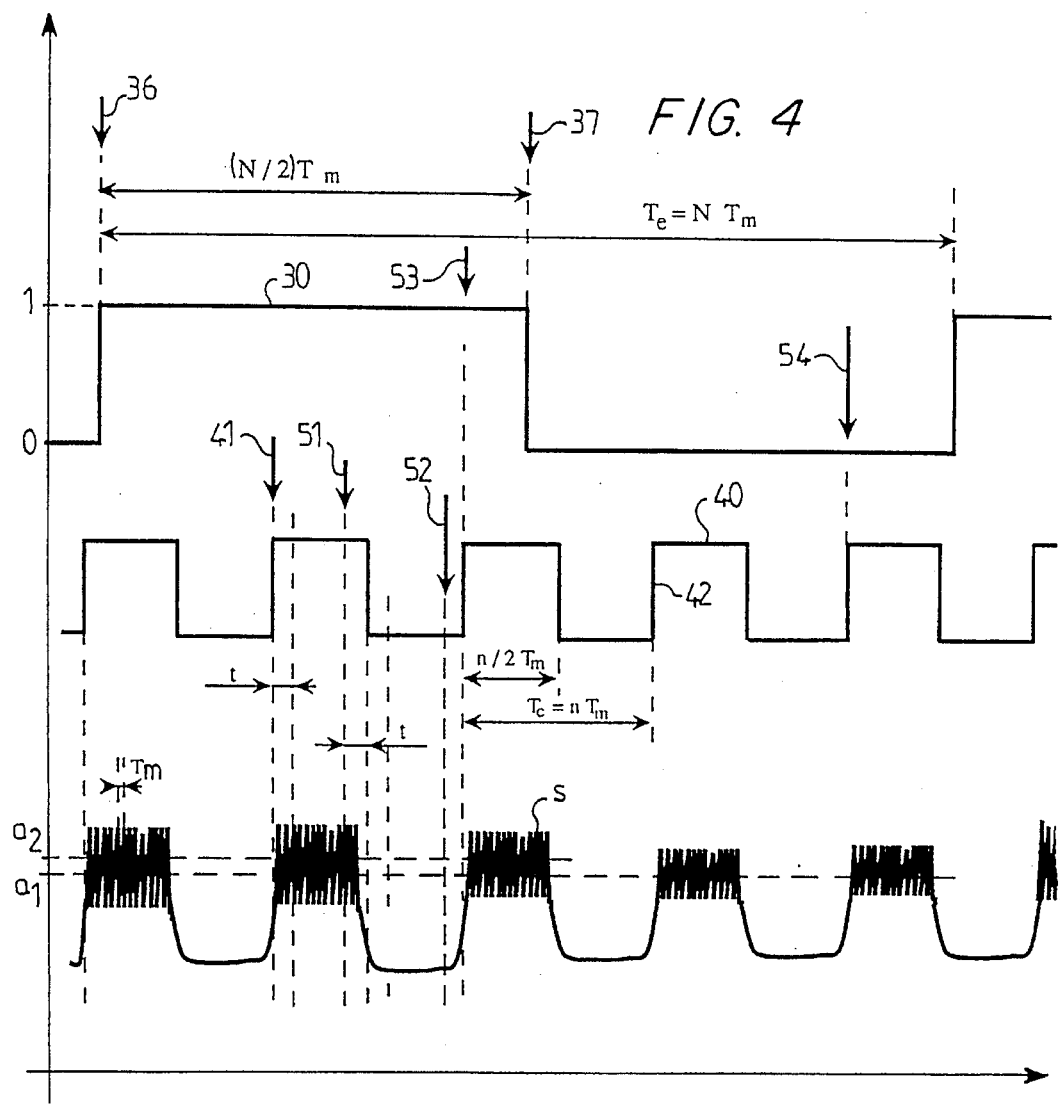
FIG. 4 is a timing diagram of the electric signal furnished by the photodetector compared to the excitation signal and switching signal in the ellipsometer of FIG. 1.

As shown in FIGS. 2 and 4, external excitation signal 30 is a periodic signal in the form of pulses of period $T_e$ and frequency $\Omega_e$. This signal is in pulse form taking alternately the value 1 on the first half of period $T_e$, followed by the value 0 on the other half of this period.

The electric signal s supplied by photodetector 13 is modulated at the modulation frequency $\omega_m$ of photoelastic modulator 6 and its average value takes two values a1 and a2 depending on whether of not sample 3 is subjected to external excitation originating from exciter 16. Modulation period $T_m$ is contained n times in excitation period $T_e$. It should be stressed that n is not necessary an integer.

As illustrated in FIG. 2, signal s from the detector is broken down into excitation significant zones 31, non-excitation significant zones 32, and transitory zones 33, 34, 35.

The duration of transition zones 34 on the one hand, and 33 and 35 on the other hand, is equal to 2 t $T_m$, where t is an integer equal to at least 1 which depends on the nature of the external excitation. Advantageously it is equal to 2.

The processing described above performed by electronic processing means 14 on signal s supplied by detector 13 via line 19 makes it possible to neutralize the values of signal s during transitory periods 33 to 35 and to use the values of the signal, respectively during excitation periods 31 and non-excitation periods 32, to obtain the values of the ellipsometric parameters, respectively in the presence and absence of excitation.

To achieve this, acquisition of significant signals is synchronized starting from the positive-going or rising transition 36 or negative-going or decaying transition 37 of switching signal 30. Starting from these edges, a number t of modulation periods of a duration $T_m$ are neutralized, then the values of signal s are acquired during a number T of modulation periods, the value being:

$$\left( \left[ \frac{\omega_m}{\Omega_e \times 2} \right] - 2t \right)$$

To control the validity of the data acquired, the state of switching signal 30 is tested and verified by the electronic processing means 14 using the phase and frequency reference signal from the switching device 17. A first test of the state of the switching signal 30 at time 51 is conducted during the t modulation periods following acquisition of the signal in the presence of excitation. It is validated when the value of switching signal 30 has been confirmed as 1 corresponding to the presence of excitation.

In a similar manner, a second test of the state of the switching signal 30 at time 52 is conducted during the t modulation periods following acquisition of the signal in the absence of excitation. It is validated when the value of switching signal 30 has been confirmed as 0 corresponding to the absence of excitation.

Contributions obtained during this acquisition of the signal, respectively in the presence and absence of excitation, are possibly cumulated, then processed conventionally at a later stage by electronic processing means to supply ellipsometric parameters $\psi_1$ and $\Delta_1$ in the presence of excitation and $\psi_2$ and $\Delta_2$ in the absence of excitation.

When the ellipsometer implemented is phase-modulated, which corresponds to the preferred embodiment of the invention, it is known that parameters ψ and Δ are accessed by breaking down the received signal s, by Fourier transform, into three components S0, S1 and S2 (not shown), respectively continuous, at the frequency $\omega_m$ and at the frequency $2\omega_m$.

Figure 3:
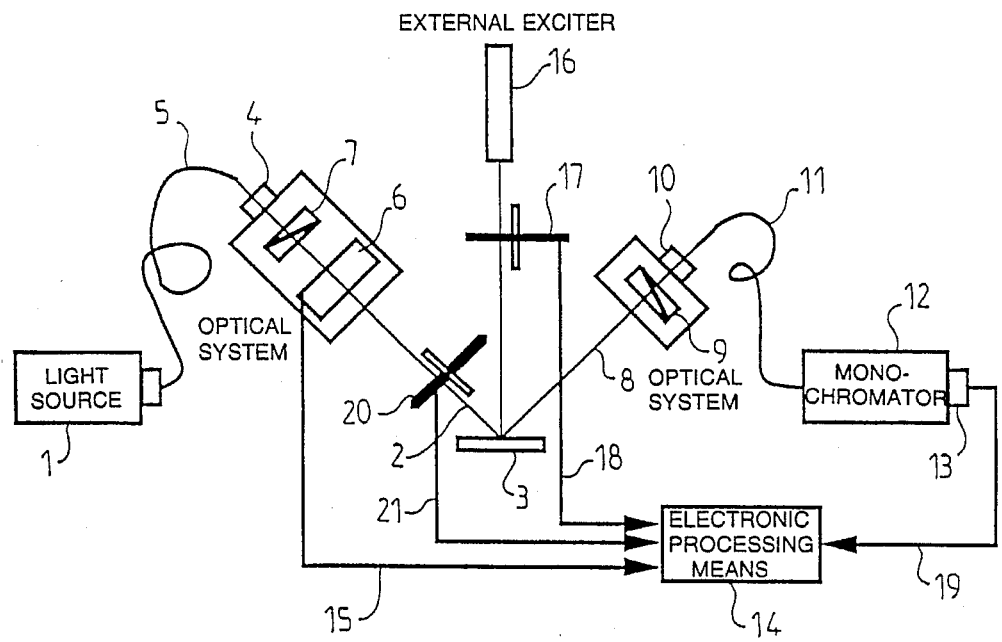
FIG. 3 is a general diagram of the ellipsometer of the invention with triple modulation.

The accuracy obtained on the continuous component S0 is improved by introducing a third modulation, such as that shown in FIGS. 3 and 4.

For this purpose, a switching device 20 is interposed on light beam 2 of the ellipsometer between the photoelastic modulator and the sample. Naturally, without substantial modifications, this switching device could be placed in any position between source 1 and detector 13.

A reference of this switching is fed to electronic processing means 14 via line 21.

The signals thus obtained are shown in FIG. 4.

The external excitation signal furnished by exciter 16 is referenced 30 and has the pulse form described earlier.

The switching signal furnished by switching unit 20 also has a pulse form 40. It has a period $T_c$ and takes the value 1 on the first half of this period and the value 0 on the second half.

Acquisition of detector signal s by electronic processing means 14 in the presence of excitation is synchronized on the positive-going or rising transition 41 of switching signal 40, after synchronization at positive-going or rising transition 36, when the value of excitation signal 30 is 1.

Starting from positive-going or rising transition 41, a number t of modulation periods is neutralized, and then acquisition performed for a duration corresponding to a number of modulation periods $T_m$ equal to:

$$\left(\left[\frac{\omega_m}{\omega_m \times 2}\right] - 2t\right)$$

In the same manner, the significant values of the signal in the absence of excitation will be acquired starting from a positive-going or rising transition 42 of switching signal 40, when the value of excitation signal 30 is 0, after synchronization at negative-going or falling transition 37.

The periods of switching device $T_c$ and of external excitation $T_e$ are such that each half-period of external excitation $T_e$ contains at least one period of switching device $T_c$.

Thus, at least one period $T_c$ of switching device 20 placed on the beam of the ellipsometer occurs during each half-period $T_e$ of excitation.

As in the preceding embodiment, tests 51 et 52 are performed on switching signal 30 of the excitation. Furthermore, similar tests 53 and 54 are performed on switching signal 40 of the ellipsometer beam.

All the values acquired in such conditions on several successive periods of the excitation signal can be accumulated and processed in order to extract the ellipsometric parameters sought.

The ellipsometer of the invention therefore allows new parameters to be obtained that are ellipsometric parameters of the sample as a function of excitation frequency, and which hitherto were virtually impossible to measure.

Furthermore, this apparatus can also be used, without modification, in conditions allowing access to parameters whose measurement is well known.

In the absence of excitation, it behaves as a spectroscopic ellipsometer thus allowing measurement of the sample's ellipsometric parameters.

In the absence of photoelastic modulation, it also allows reflectance measurements and measurements of modulated reflectance, electroreflectance, photoreflectance, etc. to be conducted.

A number of alternative embodiments of the invention can also be envisaged. In particular, external excitation signal 30 can take a null value on the first part of its period and the value 1 on the complementary period, this being the opposite to that described above. In one case like the other, the first and second parts of the period can have unequal durations.

The monochromator can also be replaced by a spectrograph which when associated with a suitable detector allows an analysis to be carried out simultaneously on several wavelengths.

What is claimed:

1. Spectroscopic ellipsometer system modulated at a frequency $\omega_m$ intended to measure a sample, comprising:

a spectroscopic ellipsometer, equipped with electronic processing means and furnishing ellipsometric parameters; and external means for exciting the sample;

wherein:

the spectroscopic ellipsometer is phase-modulated, the means for exciting the sample produces a periodic, alternating excitation signal at a frequency $\Omega_e$, a reference signal based on the excitation signal is sent to the electronic processing means, and a measurement of said sample contains the values of the sample's ellipsometric parameters (Ψ, Δ) respectively in the presence (Ψ$_1$, Δ$_1$) and absence (Ψ$_2$, Δ$_2$) of external excitation of the sample, as a function of the excitation frequency $\Omega_e$.

2. The modulated spectroscopic ellipsometer system of claim 1, wherein said spectroscopic ellipsometer includes a photodetector whose electronic signal s is processed by the electronic processing means, said signal s defined as being divided into signal portions, said signal portions comprising periods of excitation, periods of non-excitation and transitory periods separating the excitation and non-excitation periods, the transitory periods being neutralized, and the excitation and non-excitation periods being processed to produce the ellipsometric parameters of the sample, respectively in the presence (ψ$_1$, Δ$_1$) and absence (ψ$_2$, Δ$_2$) of excitation, as a function of the excitation frequency $\Omega_e$.

3. The modulated spectroscopic ellipsometer system of claim 1, wherein the electronic processing means includes means for testing the state of excitation signals from the excitation means using the reference signal received therefrom.

4. The modulated spectroscopic ellipsometer system of claim 2, wherein the excitation frequency $\Omega_e$ is low with respect to the modulation frequency $\omega_m$, the electronic processing means is synchronized on the excitation frequency, and the electric signal of the photodetector is acquired by the electronic processing means after a first set of t modulation periods where t≧1 and t is a whole number, starting from a rising transition of the excitation signal during a number T of modulation periods to produce the ellipsometric parameters in the presence of excitation, then after a second set of t modulation periods, starting from a falling transition of the excitation signal during the number T of modulation periods to produce the ellipsometric parameters in the absence of excitation, the value of T being:

$$\left(\left[\frac{\omega_m}{\Omega_e \times 2}\right] - 2t\right)$$

5. The modulated spectroscopic ellipsometer system of claim 4 wherein said electronic processing means includes means for testing the level of the excitation signals with each rising transition and falling transition of the excitation signal.

6. The modulated spectroscopic ellipsometer system of claim 1 wherein the spectroscopic ellipsometer includes a light beam source, said source generates a light beam having a switching frequency $\omega_c$ between the ellipsometer's modulation frequency $\omega_m$ and the excitation frequency $\Omega_e$, and a reference signal based on the switching frequency is sent to the electronic processing means.

7. The modulated spectroscopic ellipsometer system of claim 1 wherein the excitation of the sample is luminous.

8. The modulated spectroscopic ellipsometer system of claim 1 wherein the excitation of the sample is electric.

9. The modulated spectroscopic ellipsometer system of claim 1 wherein the excitation of the sample is magnetic.

10. The modulated spectroscopic ellipsometer system of claim 1 wherein the modulation frequency $\omega_m$ of the ellipsometer is in the order of 50 kHz and the excitation frequency $\Omega_e$ in the order of 5 kHz.

11. The modulated spectroscopic ellipsometer system of claim 6 wherein the modulation frequency $\omega_m$ of the ellipsometer is in the order of 50 kHz, the excitation frequency $\Omega_e$ in the order of 1 kHz, and the switching frequency in the order of 5 kHz.

12. Spectroscopic ellipsometer system modulated at a frequency $\omega_m$ intended to measure a sample, comprising:

a spectroscopic ellipsometer, equipped with electronic processing means and furnishing ellipsometric parameters;

external means for exciting the sample;

wherein the spectroscopic ellipsometer is phase-modulated, the means for exciting the sample produces a periodic, alternating excitation signal at a frequency $\Omega_e$, a reference signal based on the excitation signal is sent to the electronic processing means, and a measurement of said sample contains the values of the sample's ellipsometric parameters ($\psi$, $\Delta$) respectively in the presence ($\psi_1$, $\Delta_1$) and absence ($\psi_2$, $\Delta_2$) of external excitation of the sample, as a function of the excitation frequency $\Omega_e$; and a photodetector whose electric signal s is processed by the electronic processing means, said signal s being defined as divided into signal portions, said signal portions comprising periods of excitation, periods of non-excitation and transitory periods separating the excitation and non-excitation periods, the transitory periods being neutralized, and the excitation and non-excitation periods being processed to produce the ellipsometric parameters of the sample, respectively in the presence ($\psi_1$, $\Delta_1$) and absence ($\psi_2$, $\Delta_2$) of excitation, as a function of the excitation frequency $\Omega_e$;

the electronic processing means includes means for testing the state of the excitation signals from the excitation means based on the reference signal received therefrom, the excitation frequency $\Omega_e$ is low with respect to the modulation frequency $\omega_m$, the electronic processing means is synchronized on the excitation frequency, and the electric signal of the photodetector is acquired by the electronic processing means after a first set of t modulation periods where $t \geq 1$ and t is a whole number, starting from a rising transition of the excitation signal during a number T of modulation periods to produce the ellipsometric parameters in the presence of excitation, then after a second set of t of modulation periods, starting from a falling transition of the excitation signal during the number T of modulation periods to produce the ellipsometric parameters in the absence of excitation, the value of T being:

$$\left(\left[\frac{\omega_m}{\Omega_e \times 2}\right] - 2t\right)$$

said electronic processing means tests the level of the excitation signal with each rising transition and decaying transition of the excitation signal, and the spectroscopic ellipsometer includes a light beam source, said source generating a light beam having a switching frequency $\omega_c$ between the ellipsometer's modulation frequency $\omega_m$ and the excitation frequency $\Omega_e$, a reference signal based on the switching frequency being sent to the electronic processing means.

13. The modulated spectroscopic ellipsometer system of claim 12 wherein the excitation of the sample is luminous.

14. The modulated spectroscopic ellipsometer system of claim 12 wherein the excitation of the sample is electric.

15. The modulated spectroscopic ellipsometer system of claim 12 wherein the excitation of the sample is magnetic.

16. The modulated spectroscopic ellipsometer system of claim 12 wherein the modulation frequency $\omega_m$ of the ellipsometer is in the order of 50 kHz and the excitation frequency $\Omega_e$ in the order of 5 kHz.

17. The modulated spectroscopic ellipsometer system of claim 12 wherein the modulation frequency $\omega_m$ of the ellipsometer is in the order of 50 kHz, the excitation frequency $\Omega_e$ in the order of 1 kHz, and the switching frequency in the order of 5 kHz.

* * * * *